United States Patent [19]

Tell et al.

[11] Patent Number: 4,690,772
[45] Date of Patent: Sep. 1, 1987

[54] STERILANT COMPOSITIONS

[75] Inventors: Elaine N. Tell, Fort Lee, N.J.; Preston L. Veltman, Severna Park, Md.

[73] Assignee: National Medical Care, Rockleigh, N.J.

[21] Appl. No.: 740,643

[22] Filed: Jun. 3, 1985

[51] Int. Cl.$^4$ .............................................. C11D 3/48
[52] U.S. Cl. ................................... 252/106; 252/107; 252/174.14; 252/174.18; 252/DIG. 5; 424/149; 514/832
[58] Field of Search .................. 252/106, 174.14, 100, 252/174.18, 107, 94, 186.28, 187.26, DIG. 5; 514/832, 833, 840, 149, 150, 694, 714, 474; 424/149, 130

[56] References Cited

U.S. PATENT DOCUMENTS

| | | | |
|---|---|---|---|
| 2,071,091 | 2/1937 | Taylor | 167/17 |
| 2,988,514 | 6/1961 | Robson et al. | 252/187 |
| 3,065,139 | 11/1962 | Ericsson et al. | 424/130 |
| 3,124,506 | 3/1964 | Holman | 167/58 |
| 3,350,265 | 10/1967 | Rubinstein et al. | 424/130 |
| 3,585,147 | 6/1971 | Gordon | 252/187 |
| 3,749,672 | 7/1973 | Golton et al. | 252/95 |
| 3,812,254 | 5/1974 | McConnell | 514/150 |
| 3,865,726 | 2/1975 | Chibata et al. | 424/94 |
| 3,873,696 | 3/1975 | Randeri et al. | 424/153 |
| 3,912,450 | 10/1975 | Boucher | 21/54 A |
| 4,084,747 | 4/1978 | Alliger | 424/65 |
| 4,132,780 | 1/1979 | McConnell | 424/127 |
| 4,330,531 | 5/1982 | Alliger | 424/149 |
| 4,336,881 | 6/1982 | Babb et al. | 252/364 |
| 4,411,866 | 10/1983 | Kanno | 422/25 |
| 4,436,754 | 3/1984 | Jacobs | 514/694 |
| 4,473,591 | 9/1984 | Segner et al. | 426/270 |
| 4,542,015 | 9/1985 | Smakman et al. | 521/28 |

FOREIGN PATENT DOCUMENTS 1423244 2/1976 United Kingdom .
1484972 9/1977 United Kingdom .

OTHER PUBLICATIONS

Hemodialysis Neutropenia and Dialyzer Reuse: Role of the Cleansing Agent—Raymonde F. Gagnon et al., 1984 by Marcel Dekker, Inc.
Prevention of Anti-N Like Antibodies development With Nonformaldehyde Reuse Procedure—N. K. Man et al., Proc. Dialysis Transplant Forum, 1980.

Primary Examiner—Paul Lieberman
Assistant Examiner—Hoa Van Le
Attorney, Agent, or Firm—Morgan & Finnegan

[57] ABSTRACT

There are disclosed sterilant compositions having improved biocompatibility comprising a sterilant such as sodium chlorite, an acid such as citric acid, and a buffer such as sodium bicarbonate, the compositions forming an isotonic solution with pH of approximately 7.3.

The compositions are particularly useful for cleansing and sterilizing kidney hemodialysis apparatus with minimal disruption of the protein layer which forms on the internal surface of the hollow fibers of a dialysis membrane when a patient is undergoing treatment with the apparatus thus establishing improved biocompatibility between patient and apparatus. The compositions are also useful in other areas of technology, such as, for example, food and wine making technologies.

2 Claims, 6 Drawing Figures

STERILANT COMPOSITIONS

BACKGROUND OF THE INVENTION

This invention relates to sterilant compositions. More particularly, the invention relates to sterilant compositions with improved biocompatibility which may be employed in a wide variety of industrial processes where cleansing and/or sterilization of materials and apparatus are required, but which are particularly useful in the fields of medicine, food processing and wine making, where semi-permeable membranes are used. In these latter respects, compositions of this invention are eminently useful in the field of medicine, and especially that area thereof involving hemodialysis and the cleansing and sterilization of hemodialysis apparatus for reuse. Therefore, while the compositions of this invention are useful in a wide variety of areas, they are treated herein, in the interests of simplicity, in their application to the cleansing and sterilization of hemodialysis apparatus for reuse, although it is to be understood that this invention is not to be so limited.

The cleansing and sterilization of hemodialysis apparatus for reuse presents a number of problems. Initially, when the apparatus is employed to dialyze a patient, a degree of biocompatibility is established between the patient and the apparatus. For example, in a hemodialysis operation, first saline and then blood flows through the hollow fibers of the membrane of the dialysis apparatus while dialysate flows past the outside of the membrane fibers. At the commencement of the operation, the membrane is essentially in equilibrium with saline flowing through the fibers thereof and with dialysate on the other side. When blood is introduced into the system a new equilibrium relationship between fluids passing through the system and the membrane must be established. This new membrane equilibrium is completely different from the initial equilibrium established with the saline and the dialysate.

Generally, a membrane is in equilibrium with its environment when it has reached a state of ionic configuration, physical configuration, osmotic pressure, concentration gradients and hydronium ion gradients with the fluids which surround it. However, during the hemodialysis procedure the system never truly reaches an equilibrium state, but rather a quasi-steady state in which the composition of the inlet and outlet dialysate and blood changes only incrementally and only as a result of the dialysis process itself. Now, it is known that as a fluid, such as blood, containing dissolved or suspended particulates flows over a surface, such as the internal surfaces of the fibers of a hollow fiber membrane, constituents of the blood and dialysate are adsorbed on the surfaces of the device in accordance with individual entity relative adsorbtion or reaction forces. Consequently, a rolling "front" of non-adsorbed or less strongly adsorbed materials and/or reaction products forms and proceeds as a concentrated mass towards the exit of the membrane system. While this is taking place, molecules and any sufficiently small particles pass through the membrane driven by differential concentration forces and enter the dialysis fluid. In a similar manner, entities contained in the dialysate may move from the dialysate into the blood stream. Once the surface quasi-steady state is established, the latter two activities are the main concerns of the dialysis operation.

Now, as the above mentioned activities take place, a complex protein layer consisting of general proteins such as albumen, fibrinogen, and other non-immunological macromolecules, from the circulating blood, plus immunological proteins, such as complement, are laid down on the internal surfaces of the membrane fibers. The presence of this deposited protein layer improves the biocompatibility between a patient undergoing hemodialysis and the dialysis system per se by isolating the flowing blood from the possible antigens on the surfaces of the hemodialysis device. This protein layer must be treated gently, since the improved biocompatibility exhibited thereby during reuse is a direct result of the protein layer per se. It must be kept in mind, however, that the dialysis membrane and the deposited protein layer are two separate entities, although, on second and subsequent usages they act as a system. The less the disruption of the protein layer, the greater, the improvement in biocompatibility on subsequent use.

Reuse operations require that the kidney device be cleaned and disinfected. Cleaning is necessary to prevent build up of debris that would block the hollow fibers of the membrane and close the pores. Moreover, disinfection must be adequate to eliminate all spores, bacteria, viruses and fungi that may be introduced under any reasonable conditions. However, at the same time, it is necessary to conserve a high degree of biocompatibility of the system by employing reagents which minimize disturbance of the protein layer which has been laid down, thus conserving the improved biocompatibility which has been developed between the dialysis system and the patient upon reuse of the dialysis apparatus.

A known cleansing and disinfecting reagent used for cleaning and disinfecting dialyzing apparatus is formaldehyde. Formaldehyde is strongly adsorbed on the protein layer/membrane system. Formaldehyde reacts with protein in what is termed a tanning action. The use of formaldehyde has been associated with several adverse effects, such as carcinogenicity, acute hemolytic anemia, and auto-immune anemia associated with the development of anti-N-like red blood cell antibodies. Cleansers and disinfectants as used in common practice, such as a hydrogen peroxide and a product known as Chlorox (Registered TradeMark of The Chlorox Company, Oakland, Ca.) do not have these toxic effects. However, they disrupt the adsorbed protein layer.

The use of cleaning reagents, sterilants and disinfectants and the like is known in a wide variety of fields in order to cleanse, preserve and prevent deterioration or adverse effects from taking place in a given environment. However, many of the known materials of this type cannot be usefully employed in hemodialysis systems, since they might not only be destructive to the membrane and the protein layer laid down upon dialysis but also, since they might have further adverse biological effects, being incompatible with human physiology for other reasons, such as, for example, pH, acute toxicity, or mutagenicity.

At the same time that a cleansing and sterilant reagent suitable for use in hemodialysis systems which are to be reused preferably must not adversely effect or destroy the biocompatibility established by the protein layer deposited on the internal surface of the membrane fibers, such a cleansing and sterilant reagent must also provide the required cidal action. Cidal capacity is influenced by several factors, including, for example: (1) At equal sterilant concentrations, cidal action varies markedly as pH varies; (2) At equal pH, cidal action varies markedly with sterilant concentration; (3) At equal pH and/or sterilant concentration, cidal action varies markedly with time of contact of various organisms with the sterilant system; (4) Cidal action of any given sterilant or system containing the same decreases as decomposition reactions occur, thus decreasing the concentration of the sterilant available in such systems; and (5) In order to facilitate contact of cidal agent and microorganisms, the presence of surface active agents, that is, detergents, may in some cases not only be desirable, but actually required in order to facilitate contact between the cidal agents and the microorganisms present. In the latter respect, it is to be noted that a given degree of cidal action is accomplished more rapidly and at lower sterilant agent concentrations when such surface active agents are utilized. However, the use of such agents may also adversely affect the biocompatibility of the system. In cases where such detergent materials are not present, it is, in some situations, necessary to provide a physical means of contact between the cidal agent and the organisms present. The use of such detergent materials or physical means to facilitate contact between the cidal agent and the organisms present in the system adds further complexities to the system.

Dialyzer membranes are sensitive to variations in pH. Any significant excursion from a neutral pH of about 7 causes significant deterioration in the physical strength of the membranes. Many of the commercial sterilants currently used operate at highly acidic (pH less than about 5) or highly basic (pH greater than about 9) levels. This weakens the membranes; the weakening evidences itself clinically as an increase in blood leaks and in the laboratory as a decrease in burst pressure, as dealt with more fully below.

U.S. Pat. No. 4,084,747 discloses a germ killing composition produced by contacting an acid material, preferably which consists of at least about 15 percent by weight of lactic acid with sodium chlorite in aqueous media. The amount of acid in the composition must be sufficient to lower the pH of the aqueous media to less than about 7. The Patent also discloses methods of disinfecting and sanitizing, including application of either the germ killing composition per se, or the reactants which form the same, to provide in situ production thereof, to a germ carrier including substrates of various kinds as well as an enclosed air space.

U.S. Pat. No. 4,330,531 discloses a germ killing gel, a germ killing soap, a germ killing toothpaste and applicators for dispensing such germ killing compositions. The compositions include a first gel material containing sodium chlorite and a second gel material containing lactic acid in an amount sufficient to lower the pH of the aqueous media included therewith to less than about 7.

In contrast, U.S. Pat. No. 3,812,450 discloses a method for disinfecting or sterilizing medical, surgical and dental instruments or other objects with improved sporicidal compositions in liquid phase. The method is based upon the synergistic effects observed when combining non-ionic and anionic surfactants with aqueous or alcoholic glutaraldehyde solutions. The method can also be employed with ultrasonic irradiation over a wide frequency range.

U.S. Pat. No. 4,411,866 discloses an artificial organ assembly with an artificial organ with a built-in body fluid treatment mechanism, as well as a body fluid inlet port and a body fluid outlet port, filled with a liquid harmless to the human body an sealed. The assembly also includes an extracorporeal body fluid circulation mechanism which comprises a body fluid inlet line connected the the body fluid inlet port, filled with a liquid harmless to the human body and sealed. The whole assembly is hermetically vacuum-packaged and steam sterilized in a packaged state. The artificial organ assemblies include blood dialysis apparatus.

U.S. Pat. No. 3,124,506 discloses compositions of matter comprising malic acid and certain salts thereof which, when employed in a dentifrice, as a prophylactic composition for washing the nasal cavities, as a gargle, or in a perspiration odor inhibiting composition, improves the effectiveness of these various compositions for their intended purpose. As a dentifrice, the compositions are effective as tartar removing agents, antienzyme and sanitizer agents. As a nasal wash or gargle, the compositions aid in mobilizing and removing tenacious phlegm deposits from mucous linings of the mouth, nose and throat and exert a germicidal action. When employed as a deodorant, the compositions alleviate unpleasant perspiration odor and reduce perspiration.

U.S. Pat. No. 4,473,591 discloses the retention of the natural color of canned green vegetables by blanching the vegetables prior to packing in an aqueous solution of a metal ion selected from zinc and copper, the pH of the brine solutions ranging from 5.1 to 6.4.

U.S. Pat. No. 2,988,514 discloses an aqueous acidic bleaching bath having an acid pH of 1 to 7 which consists of water, a water-soluble metal chlorite selected from alkali metal chlorites and alkaline earth metal chlorites, and at least one of certain polyamines to prevent evolution of chlorine dioxide gas.

U.S. Pat. No. 3,585,147 discloses aqueous solutions containing stabilized chlorine dioxide gas dissolved therein in the form of an alkali metal chlorite at a pH between about 7 and 13 and adapted to release chlorine dioxide upon acidification to a pH of less than about 6 and having present therein a chloride of a metal selected from alkali metal and alkaline earth metals in an amount sufficient to increase the release of chlorine dioxide from the solutions.

Finally, U.S. Pat. No. 2,071,091 discloses the formation of chlorine dioxide solutions by acidification of chlorites of alkali and alkaline earth metals.

The present invention, in contrast to the above-mentioned patents, which neither recognize the problem or the need for biocompatible sterilant compositions of this type, provides suitable, biocompatible sterilant compositions which may be used in a wide variety of industrial processes where cleansing and/or sterilization are required and which are particularly useful in the reuse of hemodialysis equipment.

BRIEF STATEMENT OF THE INVENTION

In accordance with the invention, in its broadest aspects, there are provided compositions comprising an effective amount of a water-soluble sterilant material, a water-soluble acid, and a sufficient amount of a water-soluble buffer, which compositions when mixed with water provide aqueous, isotonic sterilant solutions having a pH of approximately 7.3.

THE DRAWINGS

In order to more completely understand the present invention, reference is directed to the accompanying Drawings which are to be taken in conjunction with the following description thereof and in which.

DESCRIPTION OF THE PREFERRED EMBODIMENTS

Figure 1:
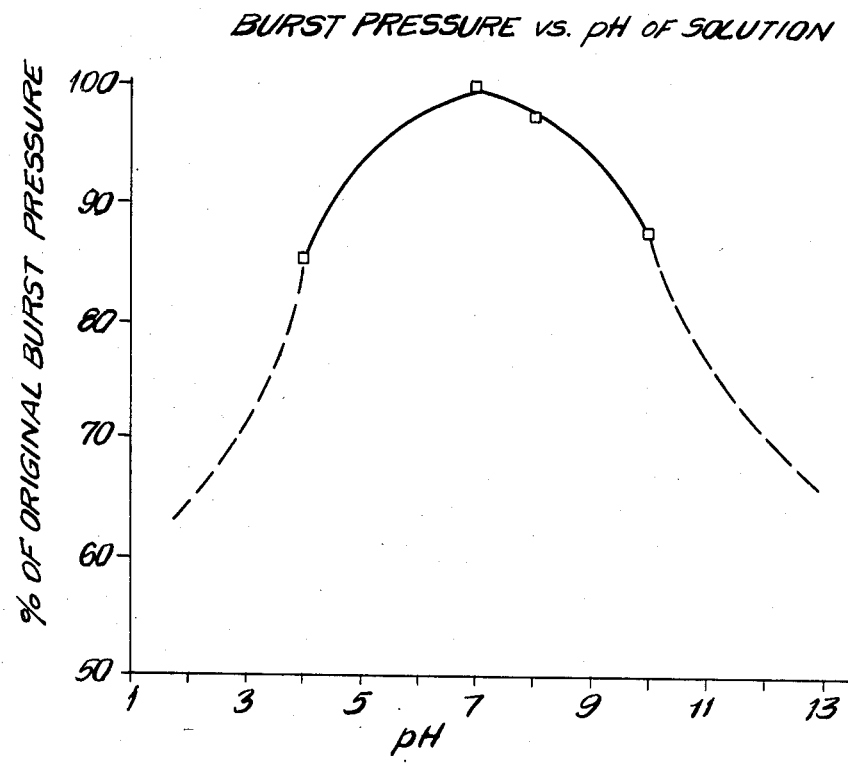
FIG. 1 is a graph illustrating the relationship between acid and alkaline treatment of a dialysis membrane and the strength thereof as reflected by the in vitro burst pressure.

In accordance with this invention, a sterilant composition compromises an effective amount of a water-soluble sterilant, a water-soluble buffer and a water-soluble acid. The sterilant may vary widely so long as it does not adversely affect the protein layer of a membrane/protein layer system. In this respect, illustrative sterilants include, but are not limited to, sodium chlorite, hypochlorous acid, ozone, aldehydes such as formaldehyde and glutaraldehyde, sodium chlorate, sodium azide, potassium permanganate and the like. Depending upon the particular sterilant used in a given composition, the effective amount thereof may also vary widely, being present in an amount at least sufficient to impart its sterilizing effect. The proportions of the composition may vary greatly depending upon the sterilant material chosen. In general, the sterilant is present in a composition in accordance with this invention in a range of from about 10 ppm (0.2 gram) to about 50,000 ppm (1,000 grams) by weight, based on the total weight of the composition. In a preferred embodiment utilizing oxidant sterilant such as sodium chlorite, the sterilant is present in a range from about 30 ppm to about 10000 ppm (200 grams) by weight is used.

Like the sterilant, the water-soluble acid employed in a composition of this invention may vary widely so long as it is water-soluble and will not adversely affect the protein layer in a membrane/protein system. It may be a water-soluble inorganic or organic acid, or acid salt. However, when an organic acid is employed, it should not be one that contains complex or high molecular weight groups that will have a tendency, when in solution, to impede the cidal action of the sterilant or be non-dialyzable. Among the acids which may be utilized in the biocompatible sterilant compositions of this invention are inorganic acids, such as hydrochloric acid, nitric acid, sulfuric acid, bromic acid and the like. Illustrative, but not limitative suitable acid salts are those such as sodium acid sulphate or sodium acid phosphate. Among suitable organic acids are lactic acid, acetic acid, ascorbic acid, citric acid, malic acid and the like. Citric acid is a preferred acid for reasons of non-toxicity and dialyzability. The amount of hydronium ion producing material, that is acid or acid salt, employed in a composition in accordance with this invention should be sufficient to adjust the pH to about 7.3. In this respect, the acid is normally present in a composition in a range of from about 100 ppm (2.0 grams) by weight to about 10,000 ppm, (200 grams) by weight, and is preferably in a range of from about 500 ppm (10.0 grams) by weight to about 1000 ppm (20 grams) by weight, based on the total weight of the composition.

As previously indicated, a water-soluble buffer is employed in the compositions of this invention. The buffer, like the acid constituent, may be inorganic or organic and may vary widely so long as it is water-soluble and will not adversely affect the protein layer in a membrane/protein systems. However, when an organic buffer is employed it should not be one that contains complex or high molecular weight groups that will have a tendency, when in solution, to (1) impede the cidal action of the sterilant or (2) to be non-dialyzable. Among the buffers which may be utilized in the biocompatible sterilant compositions of this invention are inorganic buffers, such as sodium bicarbonate, sodium phosphate, and potassium phosphate and the like. Among the suitable organic buffers are sodium acetate, potassium acetate, sodium tartrate, sodium citrate, sodium ascorbate, sodium maleate and the like. The amount of buffer employed in a composition in accordance with this invention should be sufficient when the composition is in aqueous solution to form an isotonic solution with pH of approximately 7.3, the pH of blood. In this respect, the buffer is generally present in the composition in a range of from about 20 grams to about 2000 grams by weight, and is preferably--; in a range of from about 5,000 ppm (100 grams) to about 15,000 ppm (300 grams) by weight. Physiologically isotonic solutions are defined as having a total tonicity of 0.3 osmoles per liter.

Figure 6:
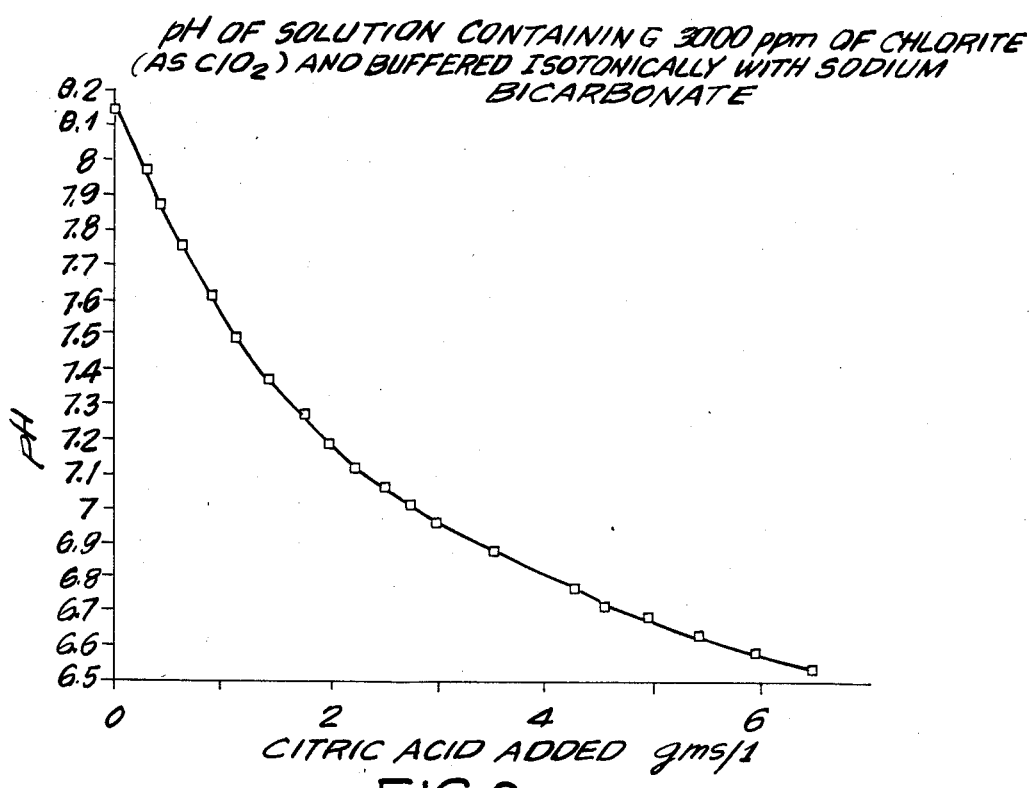
FIG. 6 is a graph illustrating that in a preferred embodiment of this invention, pH decreases smoothly as acid concentration increases.

The addition of the buffer allows the pH of the solution to remain near a pH of 7.3 even when the system is perturbed. The relative insensitivity to the addition of acid is illustrated in the graph of FIG. 6. This constant pH, equivalent to normal blood, enhances the biocompatibility of the composition, and also minimizes destructive effects on dialysis membranes.

Figure 2:
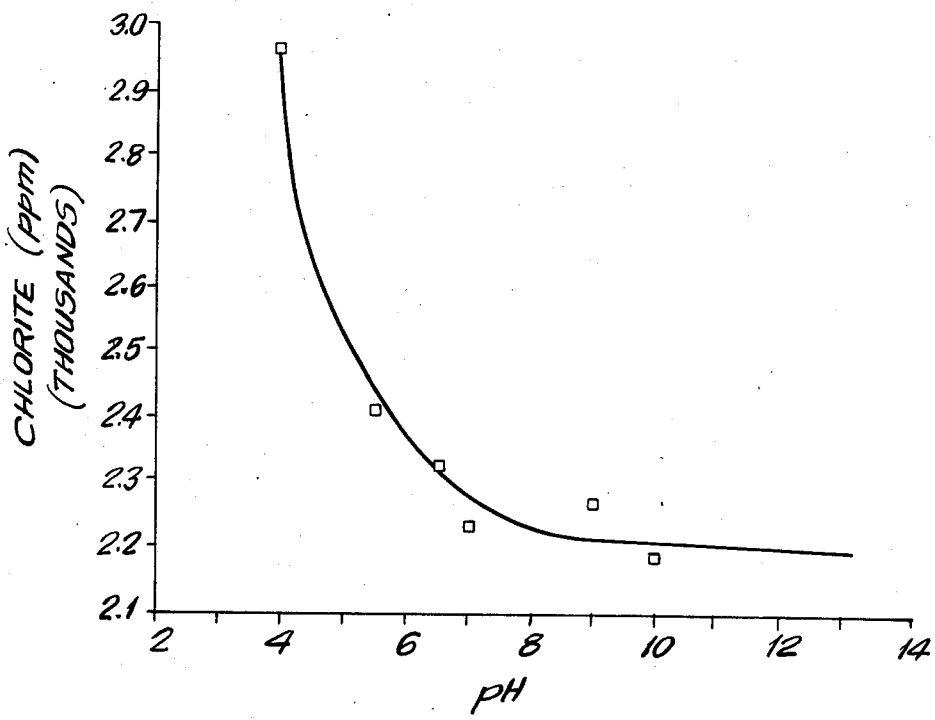
FIG. 2 is a graph illustrating the effect of pH on the availability of chlorite for a given initial chlorite concentration of a composition in accordance with the invention.

While it is possible under the most ideal conditions to provide compositions in accordance with this invention which contain only a sterilant and a suitable acid and which are isotonic and have a pH of approximately 7.3, like that of blood, such compositions tend to be unstable and less useful either in cleansing and sterilizing hemodialysis apparatus for reuse or in other areas of technology. Consequently, as a practical matter, the preferred compositions of the instant invention contain the buffer as a necessary constituent thereof in order to provide relatively long-term stable solutions. FIG. 2 and 6 illustrate the effect of pH on the availability of a sterilant moiety and the effect of acid perturbations, respectively, on a preferred embodiment of the invention.

Dialysis membranes are sensitive to variations in pH. When acidity fluctuates from approximately neutral the structure of the polymers which constitute the membranes can be altered and weakened. An illustration of this phenomenon is shown in the graph of FIG. 1, which shows the effect of pH variation on the integrity of a cellulosic membrane. Weakening is evidenced by the effect of both high and low pH on the in vitro burst strength of a hemodialyzer made of cuproammonium rayon.

As a practical matter, the compositions of this invention may be sold as either wet or dry products. In this connection, the compositions may be packaged in a two-compartment package, one compartment containing the desired amount of sterilant material and the other compartment containing the desired amount of acid, plus the buffer. The user removes the constituents from the package and simply dissolves them in the required amount of water. In another embodiment, the compositions may be provided as products in a three-compartment package, the third compartment containing the required amount of buffer separate from the acid and the user dissolves together in the required amount of water to provide an isotonic solution having a pH of approximately 7.3.

As previously mentioned, the compositions of this invention, while particularly suitable for use in the cleansing and sterilization of hemodialysis apparatus, may also be employed in other technological fields, such as food processing and wine-making. For example, in food processing, the compositions may be employed to clean and sterilize tanks, filters, heaters, chillers and lines. In the area of wine-making, the compositions may be employed to sterilize process equipment, filters, membranes, reverse osmosis equipment and the like. Moreover, when employed in technological areas other than the medical field, the choice of sterilant, acid and buffer which may be utilized will not require the stringent standards called for in the field of hemodialysis since the human body is not involved. Consequently, in such cases, and particularly where a protein layer is not involved, sterilants, acids, and buffers which may have a harsher effect on the environment in which they are employed, may be utilized. For example, sterilants such as sodium chlorate, sodium perchlorate and plutaraldehyde, acids such as hydrochloric acid, nitric acid and sulfuric acid, and buffers such as potassium phthlate, sodium tetrosalate and other industrial grade materials may be utilized in the compositions of this invention when they are employed in areas of technology other than the medical area.

It is to be understood that the term "sterilant" as employed in the instant specification and the appended claims means a material which when applied to a surface or used in a space renders that surface or space free of viable microorganisms and the term "acid" means a material which raises the hydronium ion concentration of an aqueous solution in which it is present.

THE EXAMPLES

In order to further illustrate the present invention, the following illustrative but not limitative, examples thereof are set forth. In the examples all parts and percents are by weight unless otherwise indicated.

EXAMPLE 1

A sterilant composition was prepared by mixing three grams of sodium chlorite, ten milliliters of glacial acetic acid, and 190 grams of sodium bicarbonate with sufficient water to form a total of ten liters of solution at room temperature (about 20 C.) with stirring until complete dissolution of the constituents was achieved. The solution was isotonic (0.3 osmoles per liter), had a pH of about 7.3 as determined on a Beckman pH meter, and it contained 300 ppm of sodium chlorite. The solution had a useful life greater than 30 days, and was suitable as a sterilant when assayed against *Os. aueruginosa,* using standard plating and culturing techniques.

EXAMPLE 2

A sterilant composition was prepared by mixing 300 grams of sodium chlorite, 60 grams of citric acid and 1600 grams of sodium bicarbonate buffer with sufficient water to form a total of 100 liters of solution at room temperature (about 20 C.) with stirring until complete dissolution of the constituents was achieved. The solution was isotonic, had a pH of about 7.3 as determined on a Beckman pH meter, and it contained 3000 ppm of sodium chlorite. The solution was stable for more than 30 days and was suitable for cleansing and sterilizing hemodialysis apparatus for reuse. This was demonstrated by using the solution to re-process used, contaminated, hollow fiber dialyzers. The dialyzers were flushed with solution, then filled and allowed to stand for 24 hours, at which time membrane filtration and plating were performed. There were no surviving organisms.

EXAMPLE 3

An oxidant sterilant solution was prepared by mixing 600 grams of sodium hypochlorite (as a 5% solution), 30 grams of 37% hydrochloric acid and 1900 grams of sodium acetate buffer with sufficient water to form a total of 100 liters of solution at room temperature (about 20 C.) with stirring until complete dissolution of the constituents was achieved. The solution was isotonic, had a pH of about 7.3 as measured on a Beckman pH meter, and it contained 6000 ppm of hypochlorite. This solution was tested after 12 hours as described in example 1, and found to be an effective sterilant.

EXAMPLE 4

An aqueous sterilant solution was prepared by dissolving three grams of sodium chlorite and 16 grams of sodium bicarbonate in one liter of water. Sufficient lactic acid (6 milliliters of an 85% solution) was added to this isotonic solution to bring the pH to 7.3. The solution was tested as described in Example 2 and found to be an effective dialyzer sterilant.

EXAMPLE 5

An aqueous sterilant solution was prepared by mixing three grams of sodium chlorite, 5.25 grams of acetic acid, and 113 grams of sodium bicarbonate with sufficient water to form a total of 10 liters of solution at room temperature (about 20 C.) with stirring until complete dissolution of the constituents was achieved. The solution was isotonic, had a pH of about 7.3 as measured on a Beckman pH meter, and it contained 300 ppm of sodium chlorite. This solution was tested for cidal effects against *Ps. aueruginosa* and *M. chelonei* for a 24 hour exposure time and found to be an effective sterilant. This solution was used to clean and sterilize a prototype reverse osmosis device used to reduce the ethanol content of wine. When allowed an exposure time of four hours, it was an effective sterilant in this application.

EXAMPLE 6

An aqueous sterilant solution was prepared by mixing 30 grams of sodium chlorite, 0.8 milliliter of 37% solution of hydrochloric acid, and 86 grams of sodium acetate with sufficient water to form a total of 10 liters of solution at room temperature (about 20 C.) with stirring until complete dissolution of the constituents was achieved. The solution was isotonic, had a pH of about 7.3 as measured on a Beckman pH meter, and contained 3000 ppm of sodium chlorite. This solution was tested for cidal effects against *Ps. aueruginosa* and *M. chelonei* for a 24 hour exposure time and found to be an effective sterilant.

EXAMPLE 7

An aqueous sterilant solution was prepared by mixing 30 grams of sodium chlorite, 13 grams of ascorbic acid, and 88 grams of sodium bicarbonate with sufficient water to form a total of 10 liters of solution at room temperature (about 20 C.) with stirring until complete dissolution of the constituents was achieved. The solution was isotonic, had a pH of about 7.3 as measured by a Beckman pH meter and contained 3000 ppm of sodium chlorite. This solution was tested for cidal effects against *Ps. aueruginosa* and *M. chelonei* for a 24 hour exposure time and found to be an effective sterilant. This solution was used to clean and sterilize model milk processing equipment. When allowed an exposure time of four hours, it was an effective sterilant.

EXAMPLE 8

An aqueous sterilant solution was prepared by mixing 30 grams of sodium chlorite, 45 grams of a 10% solution of nitric acid, and 88 grams of sodium bicarbonate with sufficient water to form a total of 10 liters of solution at room temperature (about 20 C.) with stirring until complete dissolution of the constituents was achieved. The solution was isotonic, had a pH of about 7.3 as measured on a Beckman pH meter and contained 3000 ppm of sodium chlorite. This solution was tested for cidal effects against *Ps. aueruginosa* and *M. chelonei* for a 24 hour exposure time and found to be an effective sterilant.

EXAMPLE 9

An aqueous sterilant solution was prepared by mixing 0.1 grams of sodium azide, 57 grams of citric acid, and 103 grams of sodium bicarbonate with sufficient water to form a total of 10 liters of solution at room temperature (about 20 C.) with stirring until complete dissolution of the constituents was achieved. The solution was isotonic, had a pH of about 7.3 as measured on a Beckman pH meter and contained 100 ppm of sodium azide. This solution was tested for cidal effects against *Ps. aueruginosa* and *M. chelonei* for a 24 hour exposure time and found to be an effective sterilant.

EXAMPLE 10

Figure 3:
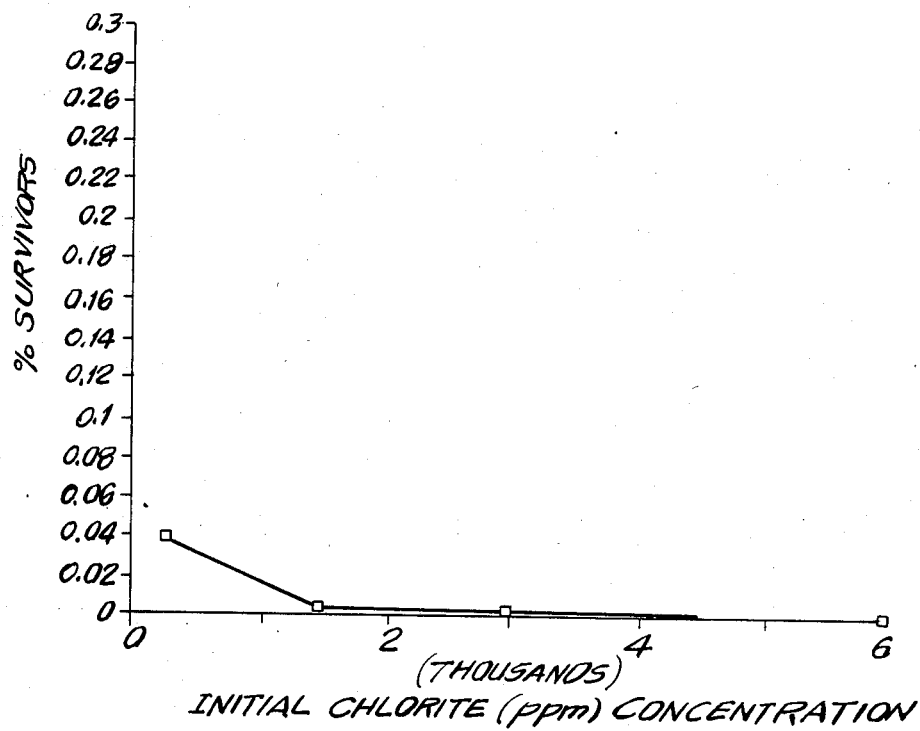
FIG. 3 is a graph illustrating the dependence of cidal power on concentration of a sterilant in accordance with the invention for a twenty-four (24) hour exposure period to varying initial concentrations of sodium chlorite in a composition of the invention.
Figure 4:
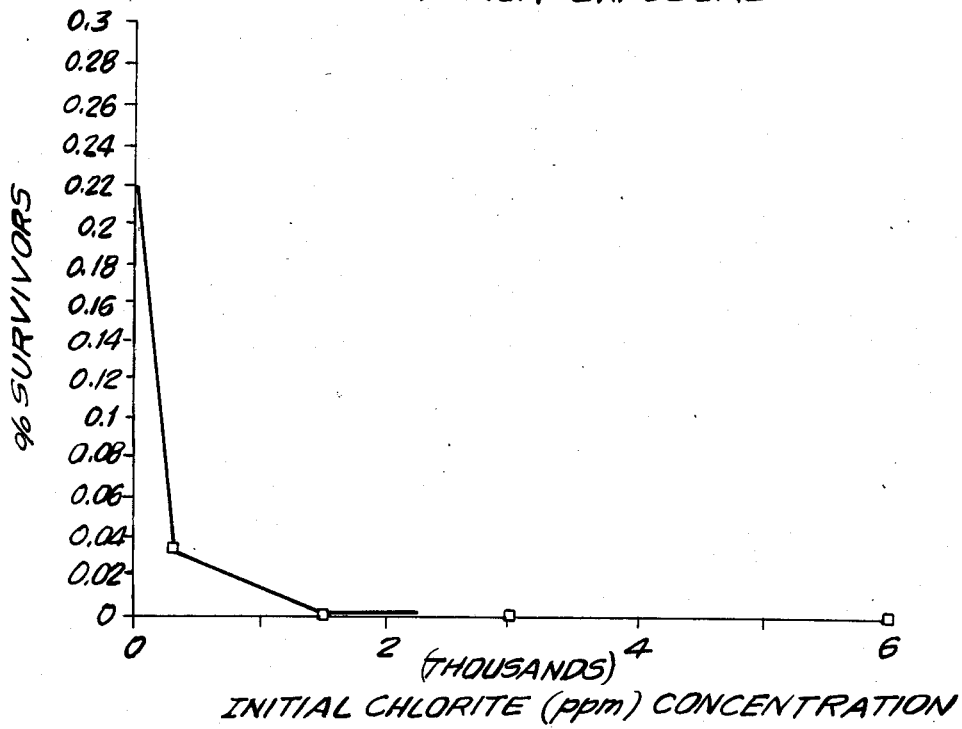
FIG. 4 is a graph analagous to FIG. 3 with the exposure time decreased to four (4) hours.

In order to illustrate the cidal activity of the compositions of this invention, *Ps. aueruginosa* was contacted with isotonic solutions having a pH of about 7.3 and consisting of citric acid, sodium bicarbonate, and 30, 300, 1500, 3000, and 6000 ppm of sodium chlorite for 4 and 24 hour incubation times. The results are summarized on the following Table and shown in the Graphs of FIGS. 3 and 4.

TABLE 1

| Chlorite Concentration | % Surviving | |
|---|---|---|
| ppm | 4 hr. Exposure | 24 hr. Exposure |
| 6000 | 0 | 0 |
| 3000 | .002 | 0 |
| 1500 | .003 | .001 |
| 300 | .038 | .034 |
| 30 | — | .210 |

EXAMPLE 11

Figure 5:
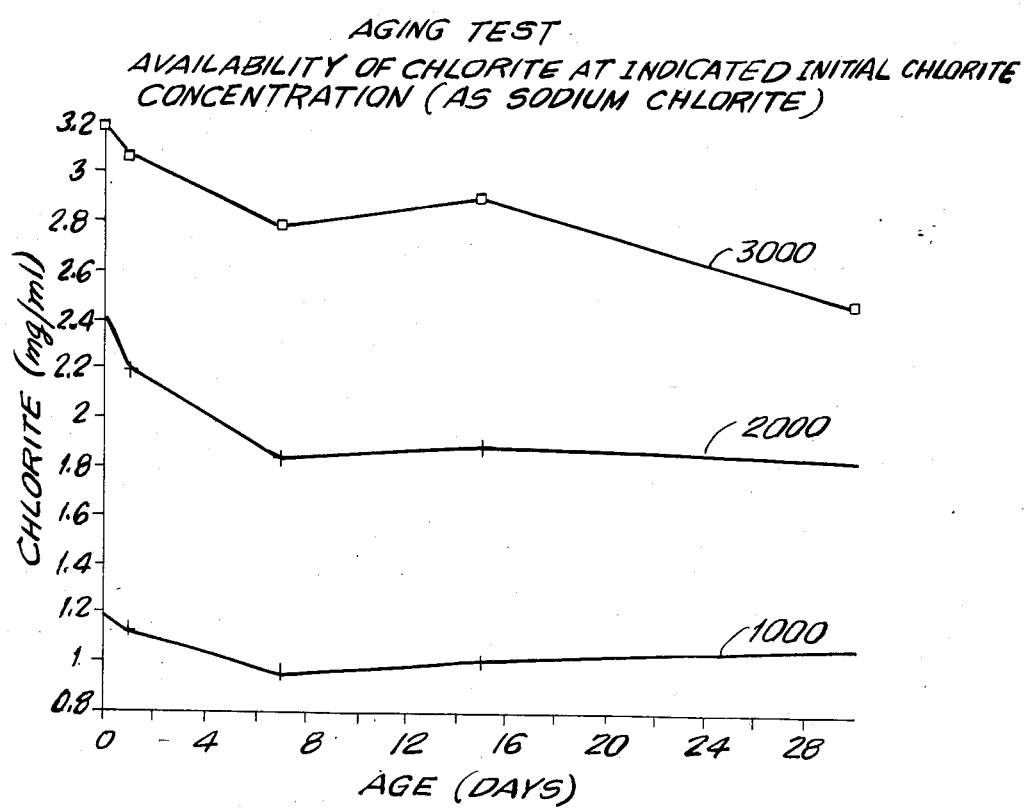
FIG. 5 is a graph illustrating the stability over a thirty (30) day aging period of several solutions in accordance with the invention employing varying concentrations of sodium chlorite, sodium bicarbonate, and citric acid.

Three solutions, A, B, and C of sodium chlorite, sodium bicarbonate and citric acid were prepared in accordance with the procedure of example 2. Each solution was isotonic, and had a pH of about 7.3. Solution A had approximately 3000 ppm, Solution B had approximately 2000 ppm and Solution C had approximately 1000 ppm of sodium chlorite. The solutions were assayed on days 0, 1, 7, 15 and 30 for available chlorite concentrations by means of the standard sodium thiosulphate assay. The results are summarized in the following Table, and shown graphically in FIG. 5.

TABLE 2

| | Day | | | | |
|---|---|---|---|---|---|
| Solution | 0 | 1 | 7 | 15 | 30 |
| A (3000 ppm) | 3.19 | 3.07 | 2.78 | 2.90 | 2.48 (m/ml) |
| B (2000 ppm) | 2.42 | 2.19 | 1.83 | 1.89 | 1.83 |
| C (1000 ppm) | 1.18 | 1.12 | .95 | 1.01 | 1.06 |

Over a period of 30 days, these solutions A, B, and C retained 77.7%, 75.6%, and 89.8% of their original chlorite concentration, respectively. For these solutions, cidal capacity in use is directly related to available chlorite concentration.

EXAMPLE 12

This Example illustrates the use of some of the compositions of this invention and the preservation of the biocompatible protein layer in a number of hemodialysis devices which had been used to dialyze a plurality of patients and are to be cleansed and sterilized for reuse.

The compositions of EXAMPLES 1, 2, 4 and 5 were employed to clean and sterilize the dialysis membranes of hemodialyzers to be prepared for reuse after the patients had been treated and had established biocompatibility with the device due to the protein layer which had been deposited on the internal surfaces of the hollow fibers of membranes of the dialyzers. The arterial blood outlet port of each hemodialyzer was connected with the dialysate inlet port thereof and the blood inlet port of each apparatus connected to a source of sterilant solution. The sterilant solution was pumped through each dialyzer in an amount of up to 10 volumes of sterilant per volume of dialyzer at a rate of approximately 100 milliliters per minute over a five to ten minute time period after which the ports were capped and the dialyzers stored for reuse.

In all cases, the protein layer remained distinguishable after the treatment and the dialyzers were completely free of microorganisms as tested by standard chemical and microbiological techniques.

The compositions of this invention present many advantages. For example, the inventive compositions can be made from materials which are relatively inexpensive and readily available through normal commercial channels. In addition, the materials are easy to employ, being readily soluble in water. Moreover, the inventive compositions exhibit excellent cidal properties and are readily prepared to provide isotonic solutions with a pH of approximately 7.3, being compatible with blood in this respect and at the same time, operative at such a physical level to achieve their intended result advantageously. Furthermore, the compositions of this invention are uniquely advantageous in the area of hemodialysis since they do not adversely affect the protein layer which is laid down on the internal surfaces of the dialysis membrane fibers during use by a patient, this protein layer establishing biocompatibility between a patient and the dialysis apparatus employed to cleanse his blood. As reported in the literature, a patient may undergo varying degrees of physical stress from minor physical discomfort to cardiac arrest when treated with dialyzers whose protein layer has been destroyed. Conservation of the improved biocompatibility established between patient and apparatus during use is of great importance and benefit.

In addition to being advantageous for the above reasons, it is also to be noted that the constituents present in the preferred compositions of this invention degrade to physiologically occurring materials such as sodium chloride and thus have no adverse effect upon the natural environment when the preferred compositions are discarded after use. Also they have no adverse effects on the patients or technicians exposed to them. Still further, due to the nature of the constituents present in the preferred compositions of this invention, the compositions are easily prepared simply by mixing and diluting in water without the need for any complex equipment to manufacture the same. The compositions of the invention are also advantageous in that they may be utilized to achieve cleansing and sterilization in a wide variety of technologies. Numerous other advantages of the compositions of the invention will be readily apparent to those skilled in the art.

While the present invention has been disclosed herein in terms of certain preferred embodiments thereof, it is understood that variations and modifications of this invention may be made without departing from the spirit and scope thereof. Accordingly, it is to be understood that this invention is not to be limited to the embodiments thereof as disclosed herein except as defined in the appended claims.

We claim:

1. A dry, granular, solid, water soluble, biocompatible, sterilant cleansing composition suitable for cleansing hemodialysis apparatus for reuse comprising by weight, 56.8 grams of sodium chlorite, 11.6 grams of citric acid and 151.4 grams of sodium bicarbonate, said composition being isotonic and having a pH of approximately 7.3 when dissolved in five gallons of water.

2. A biocompatible, sterilant cleansing solution suitable for cleansing hemodialysis apparatus for reuse comprising by weight, based on the total weight of the solution, 56.8 grams of sodium chlorite, 11.6 grams of citric acid, 151.4 grams of sodium biocarbonate, and 1892 grams of water, said solution having a sodium chlorite concentration of 3000 ppm and being an isotonic solution having a pH of 7.3.

* * * * *